United States Patent [19]

Yip

[11] Patent Number: 5,372,948
[45] Date of Patent: Dec. 13, 1994

[54] ASSAY AND REACTION VESSEL WITH A COMPARTMENTALIZED SOLUBILIZATION CHAMBER

[75] Inventor: Kin F. Yip, Elkhart, Ind.
[73] Assignee: Miles Inc., Elkhart, Ind.
[21] Appl. No.: 32,643
[22] Filed: Mar. 17, 1993
[51] Int. Cl.⁵ .............. G01N 33/72; G01N 31/22; G01N 33/546; G01N 33/539
[52] U.S. Cl. .................. 436/534; 422/58; 422/55; 422/61; 422/72; 422/82.09; 422/93; 422/102; 435/7.1; 435/7.25; 436/523; 436/531; 436/539; 436/67; 436/165; 436/169
[58] Field of Search .............. 436/518, 523, 531, 534, 436/539, 67, 165, 807, 809, 169, 533; 435/7.1, 810, 970, 7.25; 422/55, 58, 93, 102, 61, 72, 68.1, 82.09

[56] References Cited

U.S. PATENT DOCUMENTS

| | | | |
|---|---|---|---|
| 4,847,209 | 7/1989 | Lewis et al. | 436/533 |
| 4,918,025 | 4/1990 | Grenner | 436/165 |
| 4,970,171 | 11/1990 | Messenger et al. | 436/66 |
| 4,990,075 | 2/1991 | Wogoman | 422/58 |
| 5,084,397 | 1/1992 | Siddons et al. | 436/518 |
| 5,104,813 | 4/1992 | Besemer et al. | 436/179 |
| 5,162,237 | 11/1992 | Messenger et al. | 436/523 |

Primary Examiner—Esther M. Kepplinger
Assistant Examiner—Nancy J. Parsons
Attorney, Agent, or Firm—Jerome L. Jeffers

[57] ABSTRACT

Disclosed are a method and device for performing sequential analytical reactions involving a first dry reagent and a second dry reagent comprised of two or more components having different rates of solubilization. The invention enables one to fully solubilize the components of the second reagent before they are brought into contact with each other to thereby avoid interference with the reaction kinetics which result when one or both of the components are not fully dissolved prior to their being brought into contact. The invention is especially useful in conjunction with immunoassay formats involving latex bound antibodies and polymeric agglutinators.

4 Claims, 4 Drawing Sheets

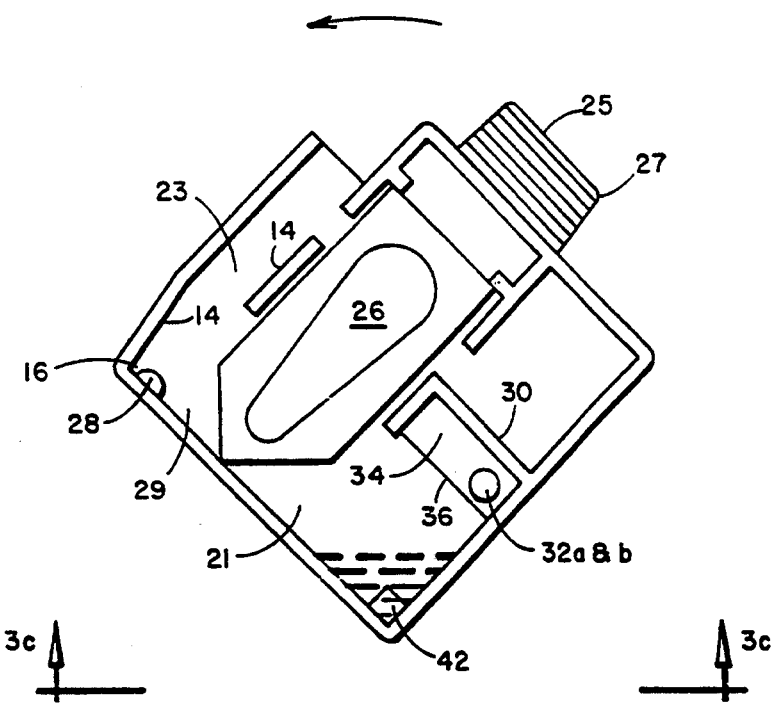
FIG. 1d
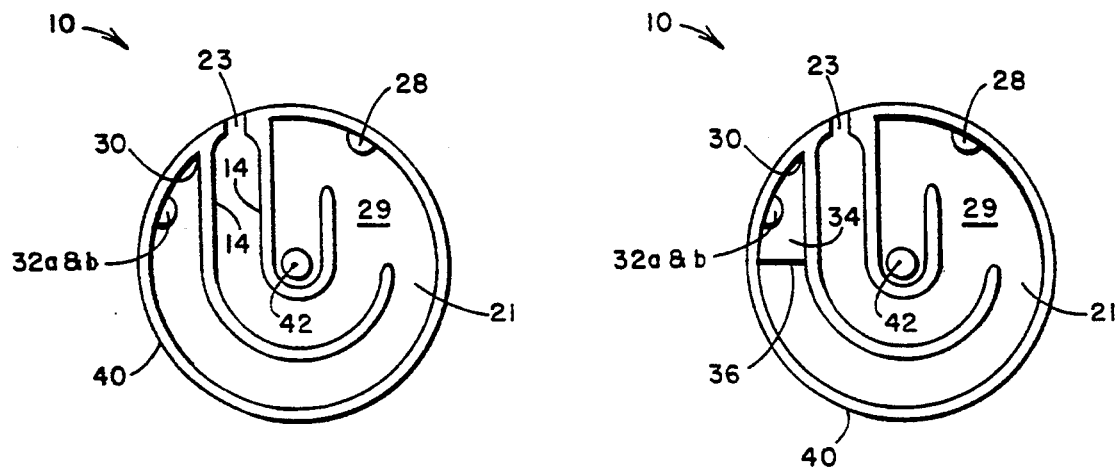
(PRIOR ART)
FIG. 2
FIG. 2a

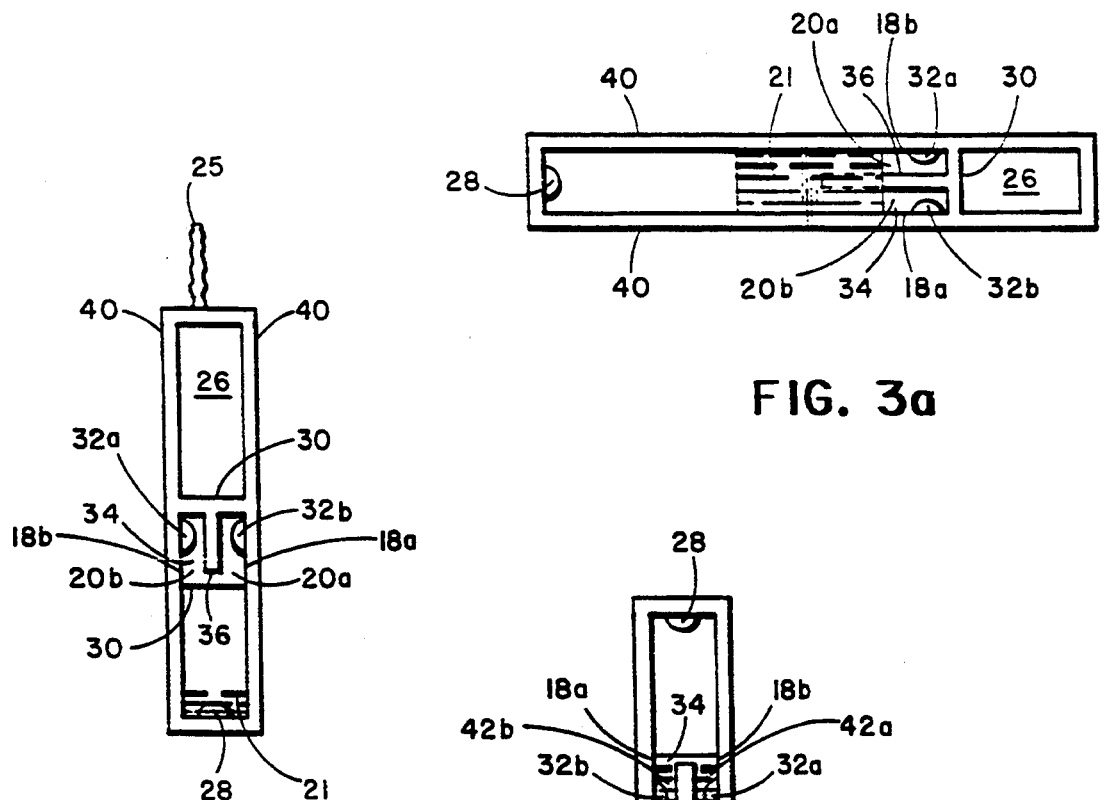
FIG. 3a
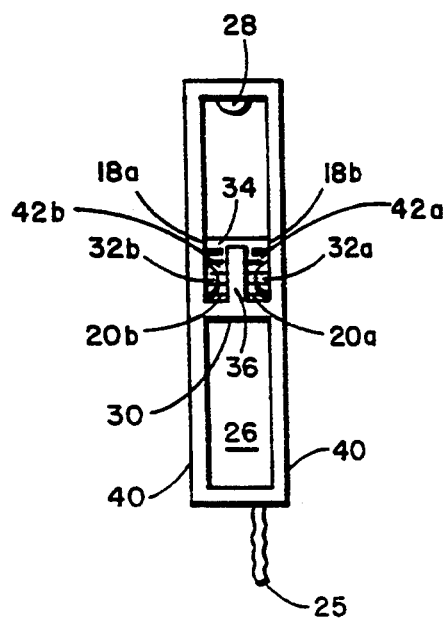
FIG. 3
FIG. 3b
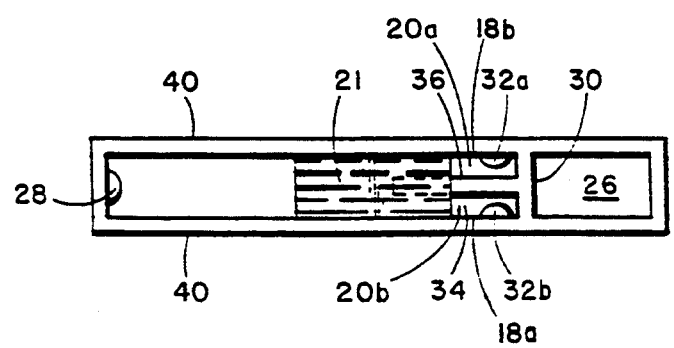
FIG. 3c

ASSAY AND REACTION VESSEL WITH A COMPARTMENTALIZED SOLUBILIZATION CHAMBER

BACKGROUND OF THE INVENTION

The present invention relates to an analytical assay procedure for determining the amount of an analyte present in a liquid test sample. In particular, the present invention relates to the determination of an analyte in a liquid test sample involving analytical reactions between the analyte and one or more analytical reagents requiring sequential manipulative steps to make such determination.

In U.S. Pat. No. 4,990,075 there is disclosed a self contained analytical reaction vessel or device and method for performing analytical assay procedures involving sequential analytical reactions between an analyte in a liquid test sample and one or more analytical reagents which interact with the analyte to produce a detectable response as a function of the analyte. The device is described as being particularly useful for performing immunoassays which typically require a number of cumbersome manipulative steps such as pipetting, mixing and incubation of the liquid test sample with the analytical reagents.

More particularly, this device is described as comprising a closed container having a substantially horizontal axis of rotation and an analytical reagent reaction channel, liquid test sample delivery means for facilitating the flow of a liquid test sample into the reaction channel. The analytical reaction channel comprises one or more reaction zones incorporated with one or more analytical reagents in the dry form. A first analytical reagent is incorporated into the first reaction zone and a second reagent or reagents into the second reaction zone which is in liquid communication with the first reaction zone. A liquid test sample disposed in the reaction channel can be transported by gravity along the reaction channel between the reaction zones by rotating the device along its horizontal axis of rotation. This device works well when only one reagent is in the second reaction zone since after dissolution of the first analytical reagent the device is simply tilted to bring the reaction fluid into contact with the second dry reagent in the second reaction zone and allowed to remain in this configuration until the second reagent completely dissolves. However, in certain analytical procedures, there must be two or more dry reagents in the second reaction zone. When these reagents have different rates of dissolution, and are being dissolved simultaneously in the same fluid, certain problems are encountered. For example, if the dissolution rates of the two reagents are slow and the reaction kinetics are fast, most of the reaction will have been completed before all of the reactants are dissolved thereby interfering with the measurement of the initial kinetics of the reaction, which are the most sensitive part thereof.

In U.S. Pat. No. 4,970,171 there is disclosed an analytical method for determining glycosylated hemoglobin wherein the amounts of both total hemoglobin and glycosylated hemoglobin derivative are measured and related as a percentage. In this method, a blood sample is treated with a thiocyanate salt and an oxidant to denature the hemoglobin in the sample thereby converting it to met-hemoglobin. The met-hemoglobin is measured spectrophotometrically to give the total amount of hemoglobin in the sample while the denatured glycosylated hemoglobin can be measured by immunoassay. This patent describes a particle agglutination inhibition assay based on the specific interaction of an antibody particle reagent and an agglutinator. The antibody particle reagent comprises the antibody, or a fragment thereof, bound to a water suspensible particle, e.g. a polystyrene or other latex, and the agglutinator comprises a polymeric material bearing a plurality of epitopic binding sites for the antibody reagent. This sort of immunosassay format is well known to those skilled in this art. The above described assay for glycosylated hemoglobin is well suited for adaptation to the reaction vessel for performing sequential analytical assays. Thus, placing the dry oxidant/isothiocyanate in the first reaction zone and dissolving it in the reaction fluid containing a blood sample to thereby cause the denaturation of the blood's hemoglobin and rotating the vessel to cause the reaction fluid to come into contact with dried antibody bearing latex and agglutinator as the second reagents in the second reaction zone, facilitates the immunoagglutination assay upon dissolution of the latex and agglutinator. However, since the latex and agglutinator go into suspension at different rates, a problem can be encountered since the latex reagent dissolves much more slowly than the agglutinator, the majority of the reaction occurs before all of the reactants are dissolved. Accordingly, the initial agglutination reaction, which is the most sensitive part of the assay, cannot be measured with the maximum degree of accuracy attainable for this type of immunoassay.

It is an object of the present invention to provide a method and device which are useful for carrying out the above described sequential assay while obviating the problems associated with the dissolution of two or more analytical reagents in the second reaction zone.

The present invention is described in greater detail in the following discussion. Since the latex reagent does not form a true solution with the reaction fluid, the terms dissolution and solution as used herein are intended to include the colloidal suspension of the latex particles having antibody bound thereto as well as true solutions.

SUMMARY OF THE INVENTION

The present invention involves a method for performing sequential analytical reactions for the determination of an analyte in a test sample comprising the steps of:

(a) providing a closed analytical reagent reaction vessel having a substantially horizontal axis of rotation, which reaction vessel comprises:
  i. an analytical reagent reaction channel containing first and second reaction zones in fluid communication with each other which reaction zones are incorporated with a first dry analytical reagent in the first reaction zone and dry components of a second analytical reagent in the second reaction zone which zone is divided by one or more septa positioned therein into at least two integral solubilization chambers each of said chambers containing a component of the second analytical reagent, whereby a liquid test sample disposed in said reaction channel can be transported by gravity along the reaction channel between the first and second reaction zones into and out of the integral solubilization chambers in the second reaction zone by rotating the reaction vessel about its horizontal axis;

ii. inlet means in fluid communication with the reaction channel for introducing a liquid test sample into the reaction channel;

(b) introducing the liquid test sample into the reaction vessel through the inlet means;

(c) bringing the liquid test sample into contact with the first dry analytical reagent in the first reaction zone to solubilize the first reagent and thereby form a first reaction solution;

(d) rotating the reaction vessel about its axis of rotation in a first direction so that the first reaction solution is transported by gravity away from the first reaction zone along the reaction channel and into contact with the components of the second analytical reagent in the integral reaction chambers to form second, third and optionally additional reaction solutions which are separated from each other by the septum or septa;

(e) maintaining the second, third and optional additional reaction solutions separate from each other for a time sufficient to permit a desired amount of dissolution of the components of the second analytical reagent in the liquid test sample to take place;

(f) rotating the reaction vessel about its axis of rotation in the direction opposite to that of the first direction to thereby cause the reaction fluid bearing the components of the second analytical reagent to flow out of the integral chambers, enter the reaction channel and mix with each other so that the second, third and optional additional analytical reagents undergo a reaction with each other to provide a detectable response; and (g) measuring the detectable response.

Also included within the scope of the present invention is the reaction vessel designed for carrying out the above described method.

BRIEF DESCRIPTION OF THE DRAWINGS

FIG. 1C depicts it in the inverted position and FIG. 1D depicts the reaction vessel after it has been returned to the position it occupied in FIG. 1B.

FIGS. 2 and 2A represent another embodiment of the prior art and the improved reaction vessel of the present invention.

FIGS. 3 and 3A–3C represent views of the presently disclosed device through its sidewall during various stages (A–D) of the method of the present invention.

DESCRIPTION OF THE INVENTION

Figure 1:
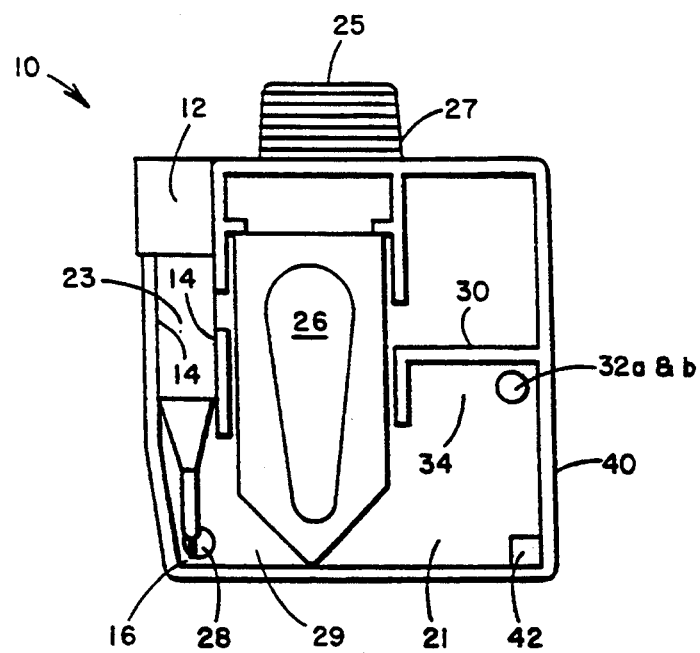
FIG. 1 represents one embodiment of the prior art reaction vessel.

Referring to FIGS. 1, 1A, 2 and 2A, the device 10 has inner walls 14 which form a delivery chamber 23 permitting the introduction of a liquid test sample, such as a small amount of blood or other biological fluid to be analyzed, into the device, and, since the delivery chamber is in fluid communication with reaction channel 21, the liquid test sample can enter the reaction channel through the delivery chamber and be caused to flow along the reaction channel by clockwise rotation of the device along its horizontal axis of rotation. The test sample is conveniently delivered through capillary dispenser 12 as depicted in FIG. 1. Since only a small amount of blood or other biological fluid will typically be introduced through delivery channel 23, additional fluid can be introduced either through the delivery channel or from another source such as liquid delivery reservoir 25 adapted to contain a buffer and/or liquid reagent for performing an analytical assay procedure. The liquid delivery reservoir comprises a reservoir body 27 having a depression therein 26 to act as fluid reservoir for holding the fluid until needed which is covered by a seal or membrane (not shown) which can be removed to allow the fluid in the reservoir 26 to flow into reaction channel 21. Simple manipulation of the device will cause the liquid test sample optionally carried by the fluid from liquid reservoir 26 to flow into the viewing zone for viewing through viewing port having transparent walls 42.

In each embodiment, the device has a first reaction zone 29, which is typically disposed in the reaction channel 21. The first reaction zone contains first analytical reagent 28 which is in the dry form and is attached to the inner wall 16 of said reaction channel or, alternatively, to one of the side walls depicted as 18a and b in FIGS. 3A and 3D. Suitable rotation of the device will bring the reaction fluid in contact with the first dry analytical reagent 28 to facilitate its dissolution therein. When first dry reagent 28 is adequately dissolved in the reaction fluid carrying the liquid test sample, the device 10 is rotated in the direction opposite to that of the first rotation to cause it to be carried by gravity out of the first reaction zone and into the second reaction zone 34 which is circumscribed by endwall 30, side walls 18a and b (depicted in FIG. 3 only) and the outer wall 40 of the reaction channel 21. Disposed in second reaction zone 34 are two separate analytical reagents 32a and b which, when dissolved in the reaction fluid, take part in a series of chemical or biochemical reactions which facilitate the detection and/or quantitation of one or more analytes suspected of being present in the biological fluid being analyzed. The reaction chamber of the devices depicted in FIGS. 1 and 2 is a single chamber in which dry reagents 32a and b dissolve in the reaction fluid while in contact with each other. As previously mentioned, this can be problematical under certain circumstances. In the device of the present invention, depicted in FIGS. 3–3C the second reaction zone 34 is divided into two integral solubilization chambers 20a and 20b by septum 36 which, when the device is rotated so as to cause the reaction liquid to be positioned in the second reaction zone 34, will prevent any intermixing of reagents 32a and 32b while they are dissolving. After the desired degree of dissolution has occurred, the now dissolved reagents 32a and 32b can be mixed by rotating the device back in the opposite direction to cause the separate reagent solutions to flow out of the reaction zone 34 and into reaction channel 21. When reagents 32a and 32b have reacted for a sufficient time to provide the desired detectable response, the reaction fluid is brought in line with viewing port 412, through which the detectable response is measured. While the drawings and foregoing description depict a single septum 36 which divides the second reaction zone into two integral solubilization chambers, there can be more than one septum included in the second reaction zone, so that the number of septa (n) will divide this zone into n+1 integral reaction chambers.

The device of the present invention is particularly useful in performing an immunoturbidimetric assay for determining the relative amount of a particular hemoglobin derivative such as the glycated hemoglobin HbAlc in a blood sample. Hemoglobin is a long lived plasma protein that couples non-enzymatically to glucose in the blood. The amount of coupled product (HbAlc) formed increases with increasing blood glucose concentration. Levels of this modified protein are thus indicative of the long term concentration of blood glucose. Such an assay as disclosed in previously mentioned U.S. Pat. No. 4,970,171 involved the steps of:

a) treating the blood sample with a thiocyanate salt to denature the hemoglobin present in the blood sample in the presence of an oxidant to convert the denatured hemoglobin to its met form;

b) assaying the denatured blood sample to determine the total amount of met-hemoglobin present therein;

c) assaying the denatured blood sample by immunoassay for the amount of hemoglobin Alc derivative present therein;

d) calculating the relative amount of hemoglobin that is in the form of glycosylated hemoglobin Alc compared to the total amount of hemoglobin present in the blood sample.

Figure 1A:
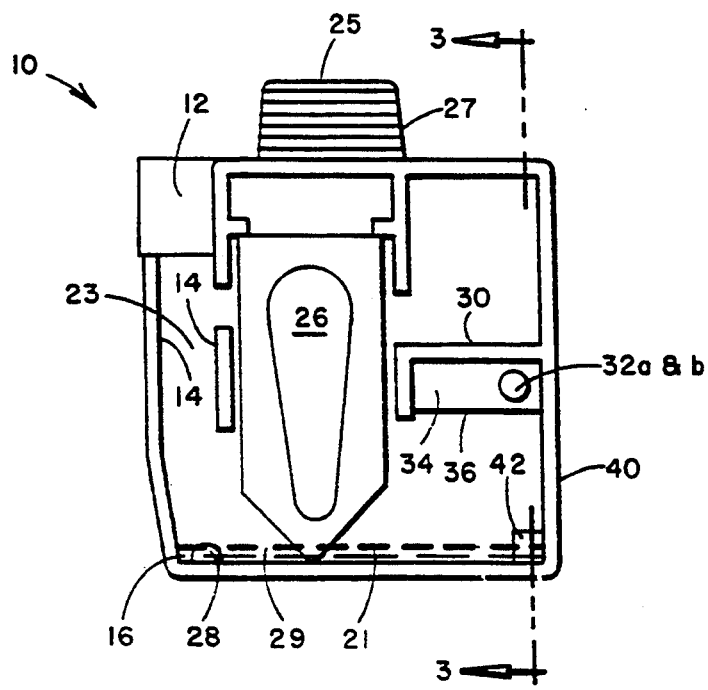
FIG. 1A depicts the improved reaction vessel of the present invention.
Figure 1B:
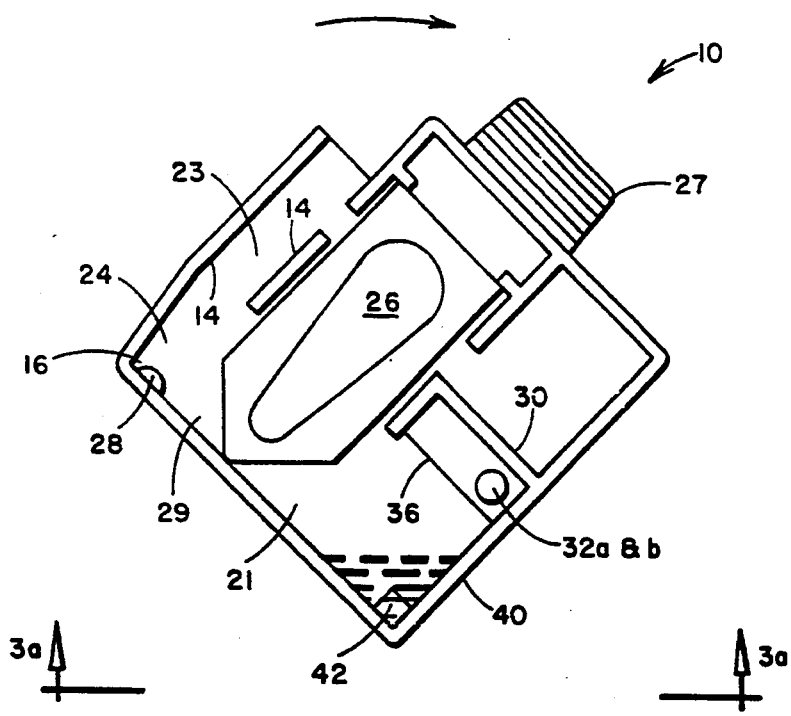
FIG. 1B depicts the reaction vessel after having been tilted 45° to the right.
Figure 1C:
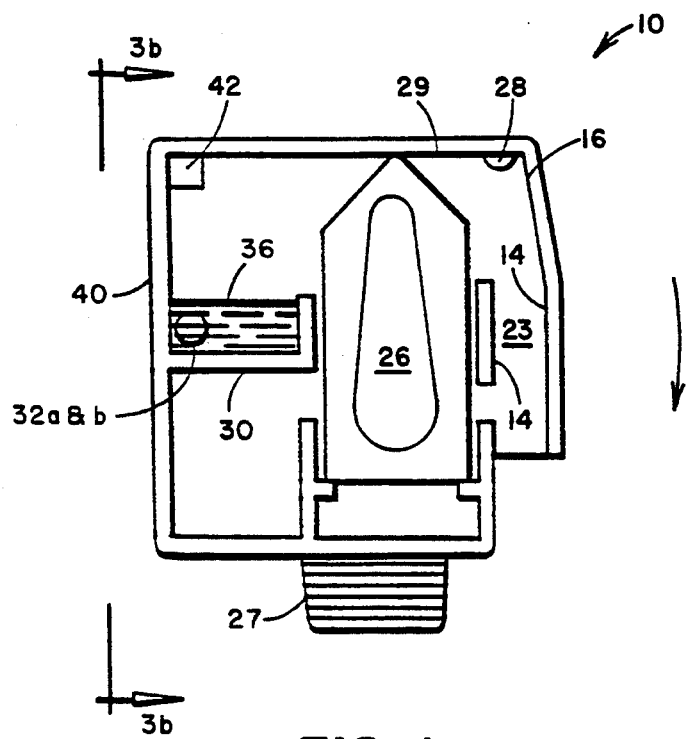

The test device of previously mentioned U.S. Pat. No. 4,990,075 is well suited for carrying out this sort of assay since the blood sample can be mixed with the thiocyanate/oxidizer in the first reaction zone and, when dissolution is complete, the resulting solution can be analyzed for total denatured met-hemoglobin and then transported to the second reaction zone where it is contacted with the reagents necessary for carrying out the immunoassay. This method works well when the immunoassay is of the ELISA type. However, when the immunoassay is of the latex bound antibody agglutination type where an antibody, or fragment thereof, specific for hemoglobin Alc is bound to a water suspensible particle (e.g. polystyrene or other latex) and the agglutinator contains a plurality of epitopic binding sites for the antibody, the previously described difficulties are encountered due to the varying of the dissolution rates of the latex bound antibody and the agglutinator which are predisposed in the second reaction zone. The problems associated with the differential dissolution rates is eliminated by the present invention. FIGS. 3 and 3a–3c represent a view of second reaction zone 34 of the present invention taken through its bottom wall 40. The following description of the method and device of the present invention involves the determination of hemoglobin Alc in a blood sample using the latex bound antibody/agglutinator immunoassay technique. Referring to FIG. 1a, a drop of blood to be analyzed is introduced into the device 10 via capillary dispenser 12 through delivery channel 23 and the reagent fluid comprising lithium thiocyanate in a glycine buffer solution is introduced by removing the covering layer (not shown) from the fluid reservoir 26 to provide a solution of the blood sample in the reaction fluid. The fluid is brought in contact with the first dry reagent 28 which is a ferricyanide salt as oxidant which in combination with the thiocyanate causes denaturation of the hemoglobin and its conversion to denatured met-hemoglobin. After sufficient time for dissolution of the ferricyanate/thiocyanate with the resulting denaturation of the hemoglobin has passed (typically about two to five minutes) the device is rotated 1/8 turn clockwise to cause the reaction fluid to cover viewing port 42. At this point a measurement of total met-hemoglobin is taken such as by measuring the reaction fluid's absorbance at a wavelength of 540 nm. After taking this measurement, the device is rotated another 3/8 turn clockwise to cause the reaction fluid to flow into the second reaction zone 34 which is divided into two solubilization chambers by septum 36 located in the middle of the reaction zone. Referring to FIG. 3, there is depicted a septum 36 and the reagent components 32a (the latex bound antibody) and 32b (the agglutinator) deposited in the two separate solubilization chambers 20a and b of the second reaction zone 34.

In FIG. 3B there is represented the reaction fluid being delivered toward the second reaction zone 34 but before reaching the septum 36. FIG. 3C represents the liquid reagent having flowed past the septum 36 and into the solubilization chambers 20a and 20b. One chamber is enclosed by the walls 36, 18a and 30 and the second chamber is enclosed by the walls 36, 18b and 30. One portion of the reaction fluid dissolves reagent component 32a to give a solution 42a while the other portion of the liquid dissolves reagent component 32b to give solution 42b. Since the solubilization of the two reagent components occurs separately in the integral chambers, no mixing of the two components takes place at this stage. FIG. 3C represents the device having been rotated 3/8 turn in a counter clockwise direction thereby causing the reaction solutions 42a and 42b to flow out of the solubilization chambers into the reaction channel 21 where they mix to form a homogenous reaction mixture. In the case of the agglutination immunoassay for hemoglobin Alc under consideration, the homogenous reaction mixture will undergo a reaction with the HbAlc analyte in which the analyte will compete for the epitope sites on the agglutinator with the HbAlc antibody bound to the latex. Since the analyte concentration and degree of agglutination will be in an inverse relationship, the higher the concentration of analyte the less agglutination will occur. By measuring the degree of agglutination, such as by well known nephelometric or light density techniques, an accurate measurement of the analyte, hemoglobin Alc in the present case, can be made.

What is claimed is:

1. A method for performing sequential analytical reactions to determine an analyte in a liquid test sample, which method comprises the steps of:

(a) providing a closed analytical reagent reaction vessel having a substantially horizontal axis of rotation and comprising:

i. a reaction channel containing first and second reaction zones in fluid communication with each other, which reaction zones are incorporated with a first dry analytical reagent in the first reaction zone and at least two different dry components of a second analytical reagent in the second reaction zone which second reaction zone is divided by one or more septa positioned therein into at least two integral solubilization chambers, each of said chambers containing a different component of the second analytical reagent, wherein the first and second analytical reagents interact with the analyte in the liquid test sample to produce a detectable response as a function of the analyte, and wherein the second reaction zone is situated a predetermined distance away from and in fluid communication with the first reaction zone whereby the liquid test sample disposed in said reaction channel can be transported by gravity along the reaction channel between the first and second reaction zones into and out of the integral solubilization chambers in the second reaction zone by rotating the reaction vessel about the horizontal axis of rotation;

ii. a liquid test sample delivery means for providing unidirectional flow of the liquid test sample into the reaction channel; and iii. an inlet means in fluid communication with the delivery means for introducing the liquid test sample into the reaction channel;

(b) introducing the liquid test sample into the reaction vessel through the inlet means;

(c) bringing the liquid test sample into contact with the first dry analytical reagent in the first reaction zone to solubilize the first reagent and thereby form a first reaction solution;

(d) rotating the reaction vessel about the horizontal axis of rotation in a first direction so that the first reaction solution is transported by gravity away from the first reaction zone along the reaction channel and into contact with the at least two different dry components of the second analytical reagent in the integral solubilization chambers to form at least second and third reaction solutions which are separated from each other by the one or more septa;

(e) maintaining the at least second and third reaction solutions separate from each other for a time sufficient to permit a desired amount of dissolution of the at least two different components of the second analytical reagent in the first reaction solution to take place;

(f) rotating the reaction vessel about the horizontal axis of rotation in the direction opposite to that of the first direction to thereby cause the at least second and third reaction solutions to leave the integral solubilization chambers, enter the reaction channel and mix with each other so that the first and second analytical reagents undergo a reaction with each other and the analyte to provide the detectable response; and (g) measuring the detectable response and using the detectable response measurement to determine the analyte.

2. The method of claim 1 wherein the reaction vessel has a reaction viewing zone in the form of an area having transparent walls in fluid communication with the first and second reaction zones and the detectable response is measured by taking readings through the transparent walls.

3. The method of claim 1 wherein there is a single septum in the second reaction zone dividing it into two integral solubilization chambers.

4. The method of claim 1 wherein the liquid test sample is whole blood, the analyte is glycosylated hemoglobin (hemoglobin $A_{1c}$), the first dry analytical reagent is an oxidant and wherein formation of the first reaction solution further comprises addition of a solution comprising an isothiocyanate salt into the first reaction zone, the at least two different dry components of the second analytical reagent are a latex bound antibody which specifically binds to hemoglobin $A_{1c}$ and an agglutinator comprising a polymeric material bearing a plurality of epitopic binding sites for the latex bound antibody to thereby bind with the latex bound antibody, resulting in agglutination, wherein the amount of hemoglobin $A_{1c}$ in the whole blood test sample is determined by independently measuring the total hemoglobin concentration in the first reaction solution and measuring the amount of hemoglobin $A_{1c}$ in the combined at least second and third reaction solutions and calculating the percent of hemoglobin $A_{1c}$.

* * * * *